United States Patent
Jalisi

(10) Patent No.: US 7,294,356 B2
(45) Date of Patent: Nov. 13, 2007

(54) PERFORMANCE ENHANCING COATING ON INTRALUMINAL DEVICES

(75) Inventor: Marc Mehrzad Jalisi, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 135 days.

(21) Appl. No.: 10/322,236

(22) Filed: Dec. 18, 2002

(65) Prior Publication Data

US 2003/0093011 A1    May 15, 2003

Related U.S. Application Data

(60) Division of application No. 09/232,581, filed on Jan. 15, 1999, now Pat. No. 6,520,923, which is a continuation-in-part of application No. 09/098,443, filed on Jun. 17, 1998, now Pat. No. 6,387,060.

(51) Int. Cl.
- *A61L 33/00* (2006.01)
- *B05D 3/00* (2006.01)
- *A61B 5/00* (2006.01)
- *A61M 25/00* (2006.01)

(52) U.S. Cl. .......................... 427/2.24; 600/585

(58) Field of Classification Search ............. 600/585, 600/434; 427/2.24, 2.25, 2.26
See application file for complete search history.

(56) References Cited

U.S. PATENT DOCUMENTS

| | | | |
|---|---|---|---|
| 4,538,622 A | 9/1985 | Samson et al. | |
| 4,748,986 A | 6/1988 | Morrison et al. | |
| 4,917,104 A | 4/1990 | Rebell | |
| 4,925,445 A | 5/1990 | Sakamoto et al. | |
| 5,005,596 A * | 4/1991 | Yamada | 132/201 |
| 5,061,273 A | 10/1991 | Yock | |
| 5,069,217 A | 12/1991 | Fleischhaker, Jr. | |
| 5,069,226 A | 12/1991 | Yamauchi et al. | |
| 5,135,503 A | 8/1992 | Abrams | |
| 5,144,959 A | 9/1992 | Gambale et al. | |
| 5,171,383 A | 12/1992 | Sagaye et al. | |
| 5,174,302 A | 12/1992 | Palmer | |
| 5,213,111 A | 5/1993 | Cook et al. | |
| 5,230,348 A | 7/1993 | Ishibe et al. | |
| 5,238,004 A | 8/1993 | Sahatjian et al. | |
| 5,253,653 A | 10/1993 | Daigle et al. | |
| 5,259,393 A | 11/1993 | Corso, Jr. et al. | |
| 5,341,818 A | 8/1994 | Abrams et al. | |
| 5,345,945 A | 9/1994 | Hodgson et al. | |
| 5,411,544 A * | 5/1995 | Mar et al. | 607/122 |

(Continued)

FOREIGN PATENT DOCUMENTS

JP    09248703 A  *  9/1997

(Continued)

*Primary Examiner*—Max Hindenburg
*Assistant Examiner*—Jonathan Foreman
(74) *Attorney, Agent, or Firm*—Fulwider Patton LLP

(57) ABSTRACT

This invention comprises guidewires, stents and other intraluminal devices having a performance enhancing coating deposited using physical vapor deposition (PVD) or chemical vapor deposition (CVD). Preferably, a radiopaque coating comprising platinum, tungsten, iridium, tantalum or the like is deposited on a desired portion of the device. Alternatively, the performance enhancing coating is a wear resistant coating of carbides such as tungsten carbide, titanium carbide, or nitrides such as titanium nitride.

12 Claims, 3 Drawing Sheets

U.S. PATENT DOCUMENTS

| | | | |
|---|---|---|---|
| 5,460,187 A * | 10/1995 | Daigle et al. | 600/585 |
| 5,476,505 A | 12/1995 | Limon | |
| 5,506,059 A | 4/1996 | Robbins et al. | |
| 5,507,760 A * | 4/1996 | Wynne et al. | 606/159 |
| 5,514,154 A | 5/1996 | Lau et al. | |
| 5,516,336 A | 5/1996 | McInnes et al. | |
| 5,520,194 A | 5/1996 | Miyata et al. | |
| 5,588,443 A | 12/1996 | Davidson | |
| 5,607,463 A | 3/1997 | Schwartz et al. | |
| 5,628,787 A | 5/1997 | Mayer | |
| 5,630,840 A | 5/1997 | Mayer | |
| 5,636,641 A | 6/1997 | Fariabi | |
| 5,637,089 A | 6/1997 | Abrams et al. | |
| 5,647,127 A | 7/1997 | Miyata et al. | |
| 5,647,858 A | 7/1997 | Davidson | |
| 5,664,580 A | 9/1997 | Erickson et al. | |
| 5,695,111 A | 12/1997 | Nanis et al. | |
| 5,716,400 A * | 2/1998 | Davidson | 623/2.42 |
| 5,720,300 A | 2/1998 | Fagan et al. | |
| 5,720,775 A * | 2/1998 | Larnard | 607/122 |
| 5,724,989 A * | 3/1998 | Dobson | 600/585 |
| 5,725,570 A | 3/1998 | Heath | |
| 5,725,572 A | 3/1998 | Lam et al. | |
| 5,733,326 A | 3/1998 | Tomonto et al. | |
| 5,824,045 A * | 10/1998 | Alt | 623/1.15 |
| 5,824,056 A | 10/1998 | Rosenberg | |
| 5,824,077 A | 10/1998 | Mayer | |
| 5,843,166 A | 12/1998 | Lentz et al. | |
| 5,849,022 A * | 12/1998 | Sakashita et al. | 606/174 |
| 5,871,850 A * | 2/1999 | Moriguchi et al. | 428/651 |
| 5,885,238 A | 3/1999 | Stevens et al. | |
| 5,891,191 A | 4/1999 | Stinson | |
| 6,030,333 A * | 2/2000 | Sioshansi et al. | 600/3 |
| 6,093,185 A * | 7/2000 | Ellis et al. | 606/28 |
| 6,099,457 A * | 8/2000 | Good | 600/8 |
| 6,129,735 A * | 10/2000 | Okada et al. | 606/169 |
| 6,174,329 B1 * | 1/2001 | Callol et al. | 623/1.34 |
| 6,208,881 B1 * | 3/2001 | Champeau | 600/374 |
| 6,291,345 B1 * | 9/2001 | Golecki et al. | 438/659 |
| 6,520,923 B1 * | 2/2003 | Jalisi | 600/585 |
| 2002/0010505 A1 * | 1/2002 | Richter | 623/1.15 |

FOREIGN PATENT DOCUMENTS

WO   9700705   9/1997

* cited by examiner

PERFORMANCE ENHANCING COATING ON INTRALUMINAL DEVICES

CROSS-REFERENCE TO RELATED APPLICATIONS

This is a divisional application of a parent application having U.S. Ser. No. 09/232,581, filed Jan. 15, 1999, now U.S. Pat. No. 6,520,923, which is a continuation-in-part application of U.S. Ser. No. 09/098,443, filed Jun. 17, 1998, now U.S. Pat. No. 6,387,060, all of whose contents are hereby incorporated by reference.

This is a continuation-in-part application of copending application Ser. No. 09/098,443, which was filed on Jun. 17, 1998, incorporated herein in its entirety by reference.

BACKGROUND OF THE INVENTION

This invention is directed to the field of intraluminal devices having coatings which provide radiopacity or wear resistance, and, in particular, to guidewires or stents having these features.

In a typical coronary procedure a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the bare wire technique which is used primarily for rail type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed. The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location if it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al., is mounted onto the proximal portion of the guidewire which extends out of the proximal end of the guiding catheter which is outside of the patient. The catheter is advanced over the catheter, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

An important attribute for guidewires is sufficient radiopacity to be visualized under a fluoroscope, allowing the surgeon to advance the guidewire to a desired location. Unfortunately, the most suitable materials for guidewires, such as stainless steel, exhibit relatively low radiopacity. Accordingly, various strategies have been employed to overcome this deficiency. Portions of the guidewire, usually the shapeable tip, may be made from or coated with relatively radiopaque metals such as platinum, iridium, gold or alloys thereof. For example, a 3 to 30 cm platinum coil tip is frequently soldered to the distal end of the guidewire. Other intraluminal devices such as stents may make use of radiopaque gold plating. An obvious drawback of these prior art methods is the high expense and scarcity of these radiopaque metals and the difficulty and expense of manufacturing products from these materials. The requirement of both radiopacity and high strength and flexibility is likewise an impediment.

Guidewires often are used to cross hardened plaques or total occlusions. The prior art has achieved wear resistant tips, but generally only at the expense of other desirable properties. As a result, an additional important feature of guidewires is a wear resistant tip that does not otherwise constrain guidewire design.

Accordingly, there remains a need for guidewires or stents having sufficient radiopacity to allow visualization under a fluoroscope without the use of expensive metals such as platinum. Additionally, there is a need for guidewires having wear resistant surfaces. This invention satisfies these and other needs.

SUMMARY OF THE INVENTION

This invention comprises an intraluminal device having a performance enhancing coating deposited using physical vapor deposition (PVD) or chemical vapor deposition (CVD).

One aspect of the invention is an intraluminal device having a radiopaque coating applied to at least a portion of the device. In a presently preferred embodiment, the intraluminal device is a stent or a guidewire, preferably formed of stainless steel, and the coating is applied to the distal tip of the guidewire. Preferably, the radiopaque coating may comprise platinum, tungsten, iridium, tantalum, or the like.

In another aspect of the invention, a wear resistant coating comprising carbides such as tungsten carbide, titanium carbide, or nitrides such as titanium nitride is applied to an intraluminal device such as a guidewire. The invention also comprises the methods of making such intraluminal devices.

A variety of conventional guidewire and stent designs may be used, as for example the guidewires and associated devices for various interventional procedures disclosed in U.S. Pat. No. 4,748,986 (Morrison et at.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.), and stents and associated devices disclosed in U.S. Pat. Nos. 5,514,154 (Lau et al.); and U.S. Pat. No. 5,476,505 (Limon), which are hereby incorporated herein in their entirety by reference thereto.

The radiopaque or wear resistant coatings of the invention deposited onto an intraluminal device preferably have a very uniform and smooth surface. Moreover, the coating may be extremely thin for improved device performance. The hard and wear resistant coatings of the invention provide a variety of properties in addition to wear resistance, including radiopacity, bending stiffness, and solderability. These and other advantages of the invention will become more apparent from the following detailed description and accompanying exemplary drawings.

DETAILED DESCRIPTION OF THE INVENTION

Figure 1:
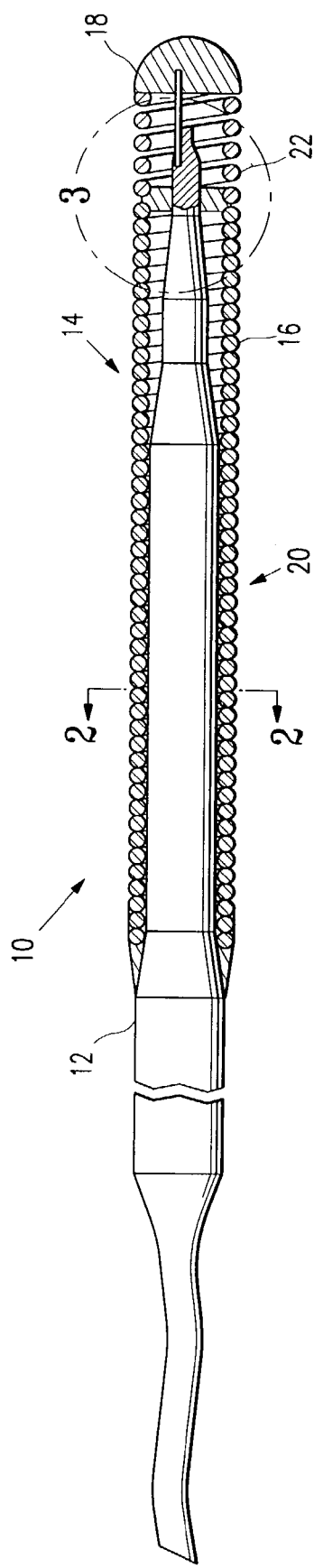
FIG. 1 illustrates guidewire of the invention with a shapeable coil tip having a performance enhancing coating.
Figure 3:
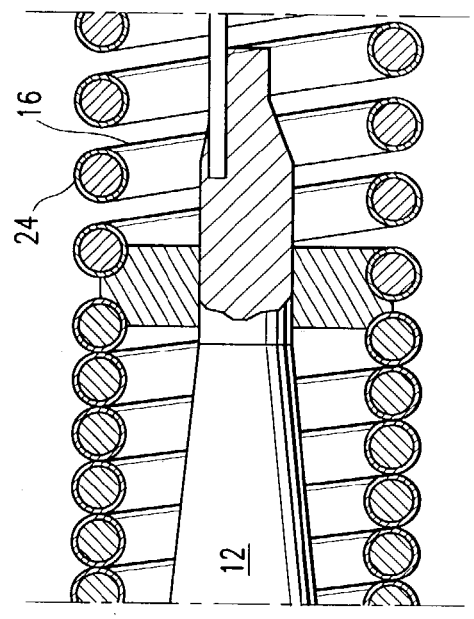
FIG. 3 is a sectional detail of the shapeable coil showing the performance enhancing coating.
Figure 2:
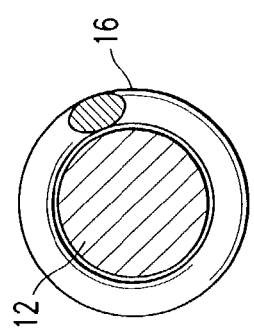
FIG. 2 is a cross section of the intermediate coil of the guidewire of FIG. 1.

FIGS. 1-3 illustrate a guidewire 10 having features of this invention that generally include an elongated core member 12 and a distal tip 14 having a performance enhancing coating on at least a portion thereof. The distal tip 14, which may be shaped or shapeable, comprises a flexible helical coil 16 and a rounded member 18 on the distal extremity, preferably formed by a solder plug securing helical coil 16 to core member 12.

In the embodiment illustrated in FIGS. 1-3, a performance enhancing coating is located on a distal portion 22 of the helical coil 16. FIG. 3 shows a detail of the distal portion 22 of helical coil 16 having uniform performance enhancing coating 24. However, various portions of the guidewire may be coated as desired. As shown in section in FIG. 2, intermediate portion 20 of helical coil 16 does not have a coating, but in alternate embodiments described below it may. In a presently preferred embodiment, the radiopaque coating 24 is located on either the distal 3 cm of the helical coil 16, or the distal 30 cm which includes the intermediate coils, depending of the physician's preference.

Suitable coatings include platinum, tungsten, tantalum, iridium and other radiopaque materials to provide radiopacity for guidewire 10. In such embodiments, the portion of the guidewire coated with the radiopaque material is typically formed from stainless steel, nickel titanium alloys or other materials that have relatively low radiopacity.

In another embodiment, the distal portion of guidewire 10 may have a coating to provide a hard, wear resistant surface. The wear resistant coating is preferably a carbide or a nitride, such as tungsten carbide, tungsten nitride, titanium carbide, or titanium nitride. In a presently preferred embodiment, the hard and/or wear resistant coating is on the distal end of the guidewire 10, which provides improved guidewire performance in applications such as the crossing of total occlusions (CTO wires). Such a hard and wear resistant coating can also provide radiopacity. Additionally, the titanium carbide, titanium nitride, and other wear resistant coatings of the invention increase the rigidity and stiffness of the substrate. This enables the coated tip of the guidewire to be shaped. For example, a NiTi alloy tip generally has poor ability to retain a bent or curved shape. In contrast, a NiTi alloy tip having a wear resistant coating of the invention would have improved bending stiffness and shape retention. Thus, a wear resistant coating having higher hardness and strength compared to the substrate, such as a stainless steel coating deposited on a NiTi substrate, provides a guidewire tip which retains a bent shape, i.e., a plastically shapeable tip.

Generally, the coating of this invention should be about 0.1 to about 15 μm thick, and preferably about 0.5 to about 10 μm. These thin coatings provide uniform coverage of the helical coil without the bridging between adjacent coils of prior art methods, which can interfere with performance. Also, the coatings of this invention have a very uniform and smooth surface, offering an improved coefficient of friction. Particularly preferred coatings include radiopaque coatings of platinum, tantalum, tungsten and wear resistant coatings of tungsten carbide or titanium nitride. Guidewires of the invention may further comprise a layer of a hydrophilic polymer. Such a hydrophilic coating over the radiopaque coating provides lubricity.

Figure 4:
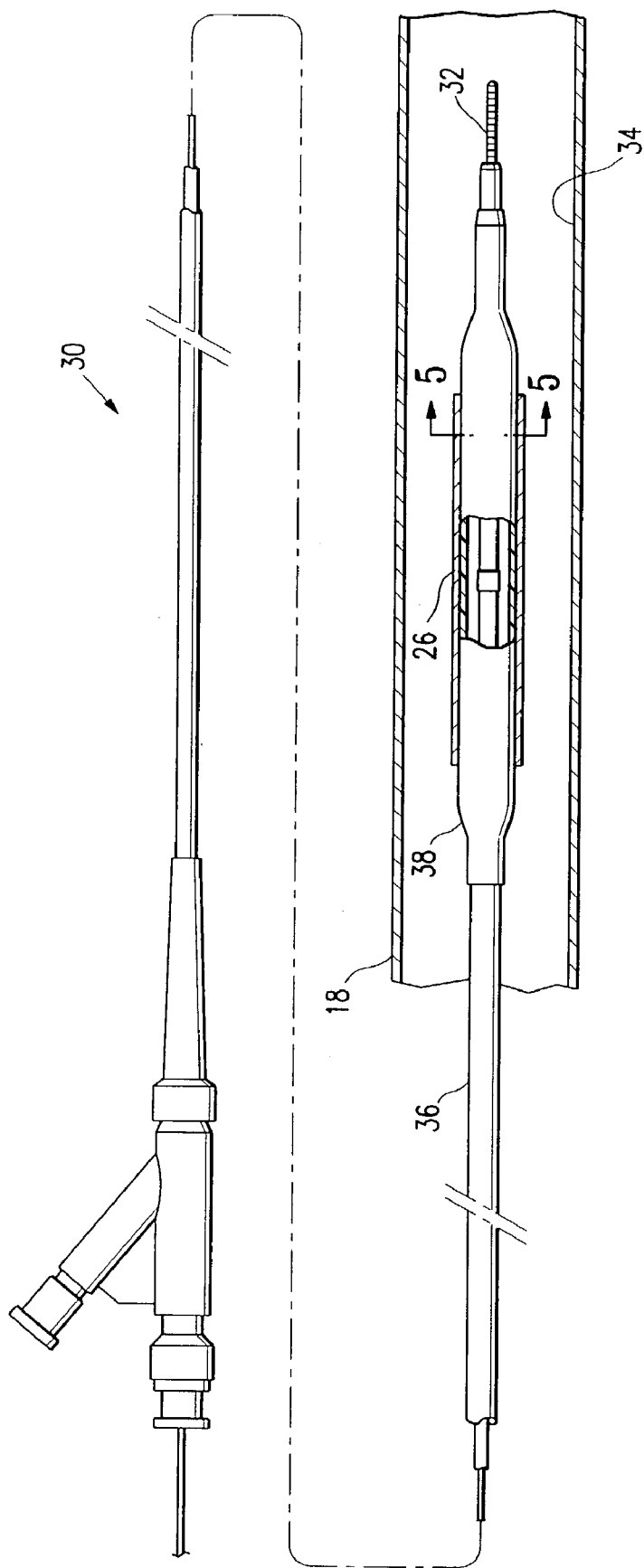
FIG. 4 shows a schematic view, partially in section, of a delivery catheter with a stent having features of the invention positioned within a body lumen.
Figure 5:
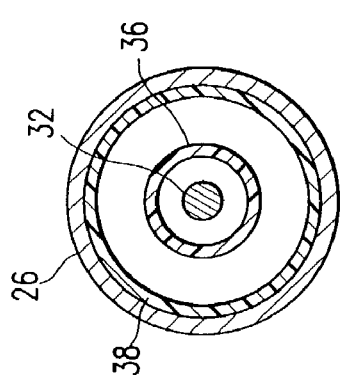
FIG. 5 is a cross section of the delivery catheter and stent assembly of FIG. 4.
Figure 6:
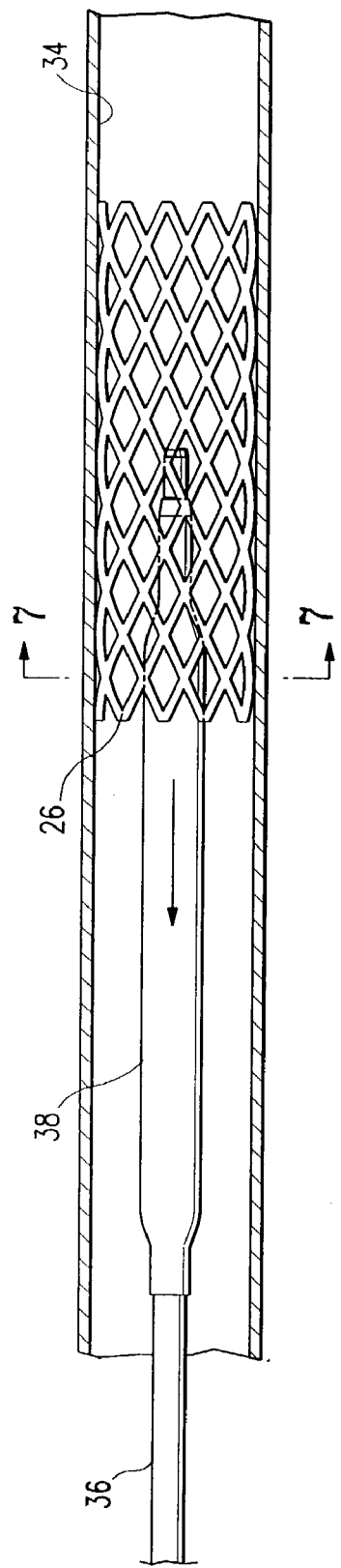
FIG. 6 is a schematic view of the stent anchored within the bodily lumen.
Figure 8:
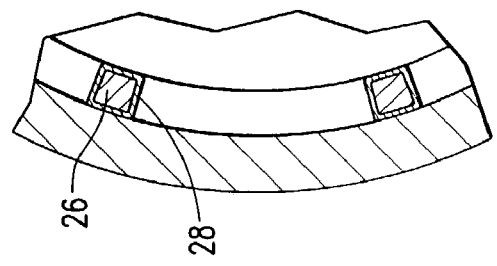
FIG. 8 is a detail view of the FIG. 7 cross section showing the performance enhancing coating.
Figure 7:
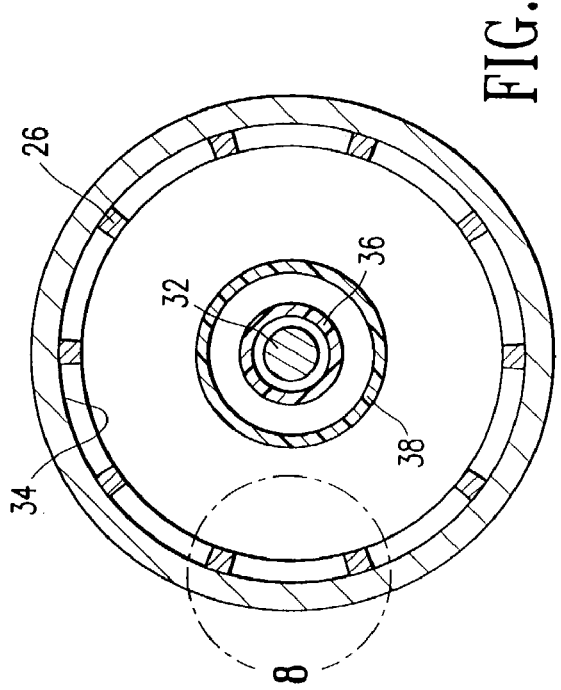
FIG. 7 is a cross section of the stent of FIG. 6.

In another embodiment of the invention, shown in FIGS. 4 through 8, a stent 26 is provided with a performance enhancing coating 28 on all or a portion of the surface. FIG. 4 is a schematic view of a delivery catheter 30 mounted over a guidewire 32 and positioned within a bodily lumen 34. Delivery catheter 30 generally comprises an elongated member 36 with stent 26 mounted on an inflatable member 38 designed to deform the stent into an expanded configuration, anchoring it within lumen 34. FIG. 5 shows a cross section of the distal portion of delivery catheter 30, with stent 26 mounted coaxially over inflatable member 38. As shown in FIG. 6, inflatable member 38 has been inflated, expanding stent 26 to anchor it within lumen 34. Inflatable member 38 is then deflated, allowing delivery catheter 30 to be withdrawn. FIG. 7 shows a cross section of expanded stent 26 anchored within lumen 34 and delivery catheter 30 with deflated inflatable member 38 being withdrawn. Finally, FIG. 8 is a detail of FIG. 7, showing performance enhancing coating 28 on stent 26.

In preferred embodiments, coating 28 comprises tungsten, iridium, tantalum or the like to give stent 26 sufficient radiopacity to be visualized under a fluoroscope. This allows the physician to confirm that stent 26 has been properly expanded and anchored within lumen 34. In other embodiments, a different coating 28 may be suitable.

Preferably, the coating 24 or 28 is applied to helical coil 16 or stent 26 by physical vapor deposition (PVD). In general, PVD involves generation of the depositing species, transport of the depositing species to the substrate and growth of the coating on the substrate. Generation of the depositing species may be achieved either by evaporation or sputtering. In evaporative schemes, thermal energy from resistance, induction, electron-beam or laser beam sources is used to vaporize the source material. Sputtering, on the other hand uses plasma ions generated by direct current or radio frequency to energize and eject depositing species from the source material (target) towards the substrate. Thus, the source material is a solid sample of the same material which is deposited to form the radiopaque or wear resistant coating, such as platinum, tungsten, iridium, tantalum (for radiopacity), or carbide or a tungsten carbide (for wear resistance). The source materials are preferably biocompatible for medical applications. Radiopaque source materials are typically high atomic weight, high density materials, thus having a high degree of atomic absorption. Source materials for the hard, wear resistant coatings, such as tungsten carbide, titanium nitride, and titanium carbide, are typically hard and often fragile materials, having a low coefficient of friction. Transport of the vaporized coating generally depends on the partial pressure of the vaporized coating; for example molecular flow occurs at low partial pressures while viscous flow occurs at higher partial pressures. Depending on the technique, the substrate may also be biased. Additionally, growth of the coating depends on the energy of the vaporized coating and substrate temperature. One of skill in the art will be able to tailor the conditions to the type of coating being applied and the substrate material.

Generally preferred conditions for PVD of a radiopaque or wear resistant coating on the distal portion of a guidewire comprise a direct current (DC) sputtering scheme with DC bias and radio frequency etch in a Alpha type vacuum chamber at about $10^{-5}$ to $10^{-9}$ Torr. The guidewires are subjected to static deposition in which the coating is first applied to one side of the wire, and then the wire is turned 180° so that the coating can be applied to the other side of the wire. The proximal portion of the guidewire should be placed in a sheath to mask it from the PVD process, exposing only the portion where coating is desired.

SPECIFIC EXAMPLES a) Parameters for Tungsten Coating on a Guidewire:
Voltage=610±5 volts DC
Power=5 kW
Sputtering Rate=2600 Å/min
Current=8.2 Amp±0.1 Amp DC A solid sample of tungsten is used as the source material. Using these parameters, 19 minutes are required to sputter a 5 μm thick coating of tungsten. Preferably, each layer of coating should be limited to about 5 μm to prevent the temperature of the substrate from rising above about 400° C. The vacuum chamber should be pumped down and subsequent layers added via additional runs if desired. Deposition thickness is linear so 10 and 15 μm thick coatings may be achieved by one or two additional runs of equivalent time. To improve adhesion, an extremely thin 0.1 μm coating may be deposited first. Similar conditions may be used to deposit tantalum radiopaque coatings.

b) Parameters for Wear Resistant Carbide Coatings on a Guidewire:
Voltage=625±5 volts DC
Power=2 kW
Sputtering Rate=80 Å/min
Current=3.15 Amp±0.05 Amp DC These parameters will sputter a 0.25 μm thick carbide coating providing superior wear resistance. As above, additional runs may be used to generate thicker coatings. A solid sample of carbide or a carbide material such as tungsten carbide is used as the source material.

The wear resistant performance enhancing coatings of this invention may also be deposited by chemical vapor deposition (CVD) processes. CVD typically involves vaporized compounds flowing over a heated substrate. The reaction of the compounds at the substrate surface deposits a film coating. Preferably, CVD should be performed at low pressures to enhance the quality of the coating.

Coatings such as tungsten carbide, titanium carbide and titanium nitride may be prepared by a one to one proportion of the tungsten or titanium metal, and the other element (e.g., carbon, nitrogen), before entering the vacuum chamber, or preferably, by using the metals as a target and introducing a reactive gas, such as methane or nitrogen, in the chamber and allowing the metal and gas to react to form the final coating materials.

The PVD and CVD processes of this invention lend themselves to automation. Accordingly, they offer a high degree of repeatability and produce a very uniform product. Further, the processes are faster and more economical than conventional methods.

The invention has been described herein primarily with reference to presently preferred embodiments comprising performance enhancing coatings applied to guidewires and stents. Other modifications and improvements can be made to the invention and such coatings may be applied to a variety of intraluminal products including electrophysiology devices, atherectomy catheters and the like without departing from the scope thereof.

What is claimed is:
1. A method of providing an intraluminal device with a radiopaque coating, comprising:
   forming an intraluminal device;
   recognizing that the intraluminal device is to include a radiopaque coating for improved radiopacity; and
   depositing a radiopaque coating having a thickness of not more than about 15 μm to at least a portion of the intraluminal device by applying the coating in a plurality of layers, each layer having a thickness of not more than 5 μm;
   wherein the coating is applied in the plurality of layers to prevent the intraluminal device from rising significantly in temperature during coating;
   wherein the plurality of layers are applied to prevent the intraluminal device from rising in temperature above 400° C. during coating;
   wherein the depositing of the radiopaque coating involves employing a voltage of 610±5 volts DC, a power of approximately 5 kW, a sputtering rate of approximately 2600 Å/min and a current of 8.2±0.1 Amp DC.
2. The method of claim 1 wherein the portion of the intraluminal device comprises a relatively thin adhesion layer of the coating and a subsequent thicker layer of the coating.

3. The method of claim 1, wherein the intraluminal device is a stent.

4. The method of claim 1, wherein the intraluminal device is a guidewire.

5. The method of claim 1, wherein the radiopaque coating is deposited by physical vapor deposition.

6. The method of claim 1, wherein the coating is selected from the group consisting of platinum, tungsten, iridium, and tantalum.

7. A method for providing radiopacity to an intraluminal device, comprising:
    providing a guidewire;
    providing a flexible helical coil;
    disposing the flexible helical coil on the guidewire; and
    after providing the flexible helical coil, applying a relatively high radiopaque coating along at least a portion of the coil, wherein the relatively high radiopaque coating includes a thickness of not more than about 15 μn, wherein the coating is applied in a plurality of layers, each layer having a thickness of not more than 5 μm;
    wherein the guide wire includes a core member and further comprising coating the core member with a radiopaque material;
    wherein the coating is applied in the plurality of layers to prevent the coil from rising significantly in temperature during coating;
    wherein the depositing of the radiopague coating involves employing a voltage of 610±5 volts DC, a power of approximately 5 kW, a sputtering rate of approximately 2600 Å/mm and a current of 8.2±0.1 Amp DC.

8. The method of claim 7, wherein the method includes coating the helical coil.

9. The method of claim 7, wherein the method includes coating the guidewire with a relatively uniform thickness and a smooth surface.

10. The method of claim 7, wherein the coating is selected from the group consisting of platinum, tungsten, iridium, and tantalum.

11. The method of claim 7, wherein less than an entirety of the coil is coated with radiopaque material.

12. The method of claim 7, wherein the plurality of layers are applied to prevent the coil from rising in temperature above 400° C. during coating.

* * * * *